United States Patent [19]
Faeser et al.

[11] Patent Number: 4,544,336
[45] Date of Patent: Oct. 1, 1985

[54] MEDICAL PERISTALTIC PUMP

[75] Inventors: Ulrich Faeser, Kronberg; Dieter Mahn, Bad Homburg v.d.H., both of Fed. Rep. of Germany

[73] Assignee: Fresenius AG, Bad Homberg, Fed. Rep. of Germany

[21] Appl. No.: 625,585

[22] Filed: Jun. 29, 1984

Related U.S. Application Data

[63] Continuation of Ser. No. 365,325, Apr. 5, 1982, abandoned.

[30] Foreign Application Priority Data

Apr. 8, 1981 [DE] Fed. Rep. of Germany ....... 3114127

[51] Int. Cl.$^4$ ...................... F04B 35/04; F04B 43/12; A61M 5/00
[52] U.S. Cl. .................................... 417/412; 417/477; 604/153
[58] Field of Search ................ 417/234, 412, 474–477; 604/153; 222/214

[56] References Cited

U.S. PATENT DOCUMENTS

| 562,903 | 6/1896 | Messmer | 417/476 X |
| 1,635,373 | 7/1927 | Lofholm | 417/477 |
| 2,434,802 | 1/1948 | Jacobs | 417/412 |
| 2,662,666 | 12/1953 | Lamport | 417/477 |
| 2,975,719 | 3/1961 | Kaufman | 417/477 |
| 4,025,241 | 5/1977 | Clemens | 417/474 |
| 4,135,647 | 1/1979 | Mascia et al. | 222/214 |

FOREIGN PATENT DOCUMENTS

| 673572 | 11/1963 | Canada | 417/476 |
| 2541892 | 4/1976 | Fed. Rep. of Germany . | |
| 2500463 | 7/1976 | Fed. Rep. of Germany . | |
| 2535650 | 2/1977 | Fed. Rep. of Germany . | |
| 2851656 | 6/1979 | Fed. Rep. of Germany | 604/153 |
| 8011213 | 4/1980 | Fed. Rep. of Germany . | |
| 2855634 | 6/1980 | Fed. Rep. of Germany | 417/477 |
| 2920975 | 11/1980 | Fed. Rep. of Germany | 604/153 |
| 2210416 | 7/1974 | France . | |
| WO80/1560 | 6/1981 | PCT Int'l Appl. | 417/477 |

Primary Examiner—William L. Freeh
Assistant Examiner—Paul F. Neils
Attorney, Agent, or Firm—Cushman, Darby & Cushman

[57] ABSTRACT

A peristaltic pump, more specially for enteral nutrition or feeding has an electric motor and a wheel, on which rollers are supported, with axis crossing the axis of the electric motor so that the main dimension of the wheel in its radial direction and the main dimension of the electric motor in its axial direction are parallel to each other or in line with each other so that a specially flat mechanical design of the pump is produced. The shaft of the electric motor has a pinion for meshing with teeth in a radial plane on the outer edge of the wheel and driving it, this producing a high step-down ratio of 1:500 or even more. The wheel with the rollers may have a generally large diameter so that it may be run at a low speed quietly. With such a diameter of the support wheel and when the pump has a flat rectangular housing, empty corners will be present in the housing on the two sides of the electric motor, into which batteries or the like may be placed. The motor may, because of the great step-down ratio, be run at a high speed so that a mass produced motor may be used for the pump. The peristaltic pump with such a flat rectangular housing may be comfortably kept under the user's clothing without making itself seen.

5 Claims, 2 Drawing Figures

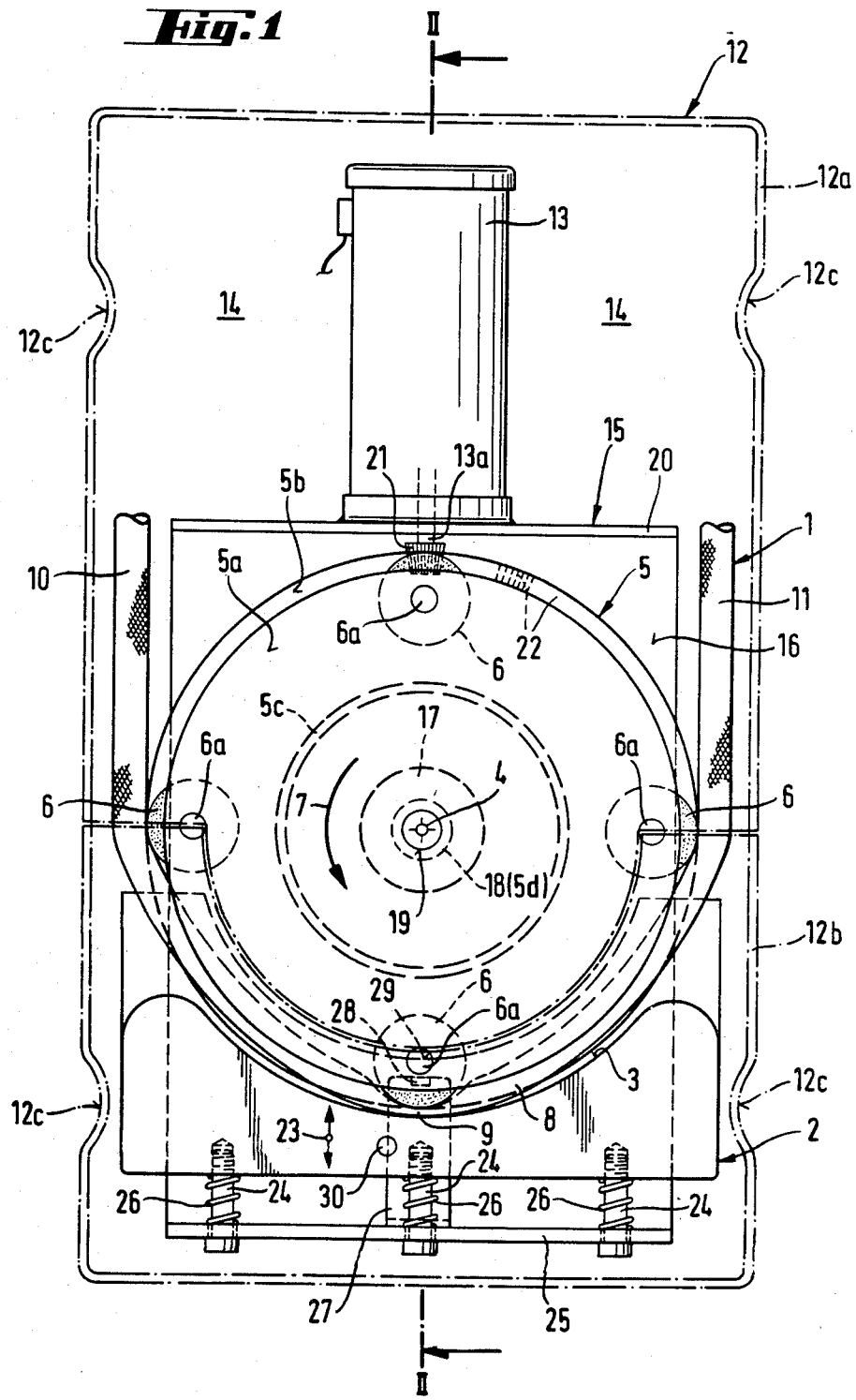

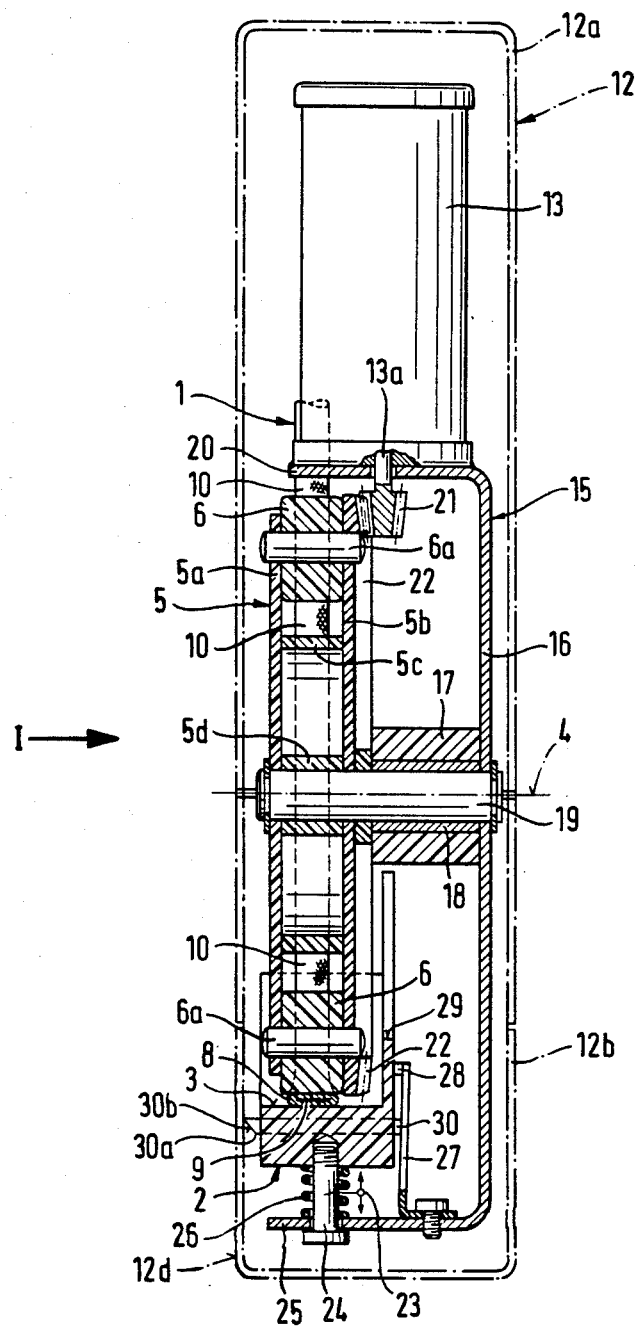

MEDICAL PERISTALTIC PUMP

This is a continuation of application Ser. No. 365,325, filed Apr. 5, 1982, now abandoned.

BACKGROUND OF THE INVENTION

The present invention is with respect to a peristaltic pump for medical purposes and more specially an enteral pump for artificial feeding with an electric motor and having a flexible pipe element acted upon by a wheel with rollers thereon for peristaltically moving material to be pumped along the pipe element by the rollers on the wheel rolling the element against a rounded backup wall, which is radially spaced from the wheel.

An example of such a peristaltic pump of the prior art may be seen for example in German Offenlegungsschrift specification No. 2,500,463, which has a generally cylindrical housing made in four pieces placed next to each other axially, that is to say a battery part, a middle part for the control systems, a motor part and a pump part next to the side, opposite to the battery part, of the motor part. The wheel with the rollers is, in this respect, normal to the axis of the electric motor and the pipe element for peristaltic pumping purposes is supported on wall parts round the rollers, such wall parts at the same time forming the wall of the cylindrical housing at the end in question.

For a generally rod-like design of the casing of this known peristaltic pump so that the pump, if made with a small overall size, may be taken around by the user with him or her, the diameter of the casing cylinder must be within a certain upper limit. Because the wheel with the rollers on its outer edge has to have a very much smaller diameter than the casing width (because, between the outer side of the casing and the rollers there is to be at least space for the pipe element and the backup wall with its support part) the wheel with the rollers necessarily has to have a very small diameter. The outcome of this is that the peristaltic pipe element has to be positioned in a curve with a generally small diameter round the edge of the small wheel, the wheel then having to be turned at a high speed to get the desired pumping rate. Such a high speed of the wheel with the rollers does, however, make for loud operation, something which is very undesired if the pump is to be taken around by the user all the time with him.

Furthermore there are undesired loading effects on the pipe element which has a very small radius, the working life of the pump then no longer being the 4000 to 5000 hours as a possible lower limit, but lower values. Lastly, the pumping function is likely to be second rate because the rollers operate against a body with a small diameter and, for this reason, there is a small spacing between the rollers, so that they are only in a position of peristaltically pumping a small amount of material between the nips between the rollers and the pipe element.

Because furthermore the wheel with the rollers thereon is fixed on the shaft of the driving motor, quite in addition to the limited amount of space on hand in the pump, a small diameter of the wheel is necessary because the speed of the motor is to be stepped down to the speed of the wheel in a single stage of gearing. Furthermore, with a small wheel diameter, the speed of the motor has to be decreased to values, which for an electric motor, are very low, for pumping at low rates. Such low motor speeds are in fact only possible with high-price special-purpose motors. Normal battery powered DC motors may not be used because they have a starting speed of about 100 rpm, this being not nearly low enough for pumping at the desired low speed, in view of the small diameter of the wheel.

Although it would be possible to have step-down gearing with coaxial input and output shafts between the shaft for driving the wheel with the rollers on the one hand and the shaft of the electric motor on the other, such gearing being for example in the form of an epicyclic system so as to give the desired step-down ratio, such a system is complex and likely to be the cause of trouble conditions. Furthermore, for using such gearing, an axial overall size of the pump would be increased because the pump part, the motor part, the control part and the battery part would have to be put one after the other in line.

On the other hand, one purpose of the present invention is that of designing a peristaltic pump of the sort noted making a flat, compact mechanical design possible without any undesired limits on the diameter of the wheel with the rollers.

For effecting this purpose, and further purposes, the axis of turning of the wheel is normal to the axis of the electric motor.

Because of the axis of the wheel being normal to that of the electric motor, the width of the wheel (its largest dimension) is parallel to the direction of the length of the electric motor, this length being the greatest dimension thereof. In a direction normal to these main dimensions it is then, for this reason, only necessary to have space for the thickness of the wheel and the thickness or the diameter of the electric motor. Separately from the question of the diameter of the wheel, a very flat design is produced so that the peristaltic pump's casing may be generally flat and rectangular, it resting flatly against the body of the user and hardly being seen if at all. The breadth of the housing is, in comparison with its thickness, hardly important so that, with respect to the diameter of the wheel with the rollers, on which the width of the housing is generally dependent, there are no further conditions to be kept to with respect to the size of the unit. For this reason, a generally large-diameter wheel with the rollers may be used without any undesired effects. With such a size of wheel, a desired pumping rate may be produced with the wheel turning at a low speed. A further outcome of this design is that the pump will be quiet in operation with exact rate control and, if the casing is block-like or rectangular, it will be possible to have room for batteries or the like on the two sides of the electric motor within the corners of the casing, such corners being otherwise empty because the wheel with the rollers is round and not rectangular. Putting it differently, the batteries or the like take up space which would not otherwise be used and do not have to be put in special parts of the casing which would make it broader or longer. Because the axes of the wheel with the rollers and of the electric motor are normal to each other, the gearing therebetween may have a very high step-down ratio of at least 1:100 and more specially more then 1:500 using a simple pinion keyed on the electric motor's shaft and running against teeth on the outer edge of the wheel. For this reason, the step-down gearing does not take up any further space.

Specially useful effects are produced if the wall supporting the pipe element against the rollers is united with a support part which may be moved in the direction of the force produced by the wheel on the pipe element, the backup wall being spring-loaded so as to be forced springingly towards the rollers on the wheel, in the way detailed in German patent application P No. 31 14 128.5 of the same applicant of even date and in U.S. application made on the same date as the present application naming the same assignee.

Useful further development of the invention will be seen in the dependent claims.

LIST OF FIGURES AND DETAILED ACCOUNT OF ONE WORKING EXAMPLE OF THE INVENTION

Further details and useful effects of the invention will be seen from the account now to be given of one working example thereof as based on the figures.

FIG. 1 is a plan view of a peristaltic pump of the present invention, its casing being marked in chained lines. FIG. 2 is a section on the line II—II of FIG. 1.

As may be seen in the figures, the peristaltic pump has as its main working parts a flexible pipe element 1, a support part 2 united with a backup wall 3 and a wheel 5 turned about an axis. At the outer edge of the wheel 5 there are four equally spaced rollers 6. On turning of the wheel 5 in the direction of arrow 7, the rollers 6 are forced one after the other against the curved working part 8 of the pipe element resting against the backup wall 3 so that, as the flexible pipe element is acted upon by one roller after the other, it is forced first by one roller 6 at a nip 9 moving with the roller 6 against the backup wall 3 so that the liquid in front of the nip 9 is peristaltically forced through the pipe element 1. The part 10, which in the present example is to be seen on the left, of pipe element 1 is joined up with an intake pipe for liquid, as for example liquid nutrient material, while the right hand end part 11 may be said to be the output connection of the pump. The end parts or connections 10 and 11 are joined up by way of sleeves or the like with the casing 12 (marked in chained lines) of the peristaltic pump so that the pipe element 1 is regularly positioned at two ends of its working part 8 and kept in the desired place inside the peristaltic pump. The end parts 10 and 11 may be joined up with unions on the outer side of the casing, and which are not detailed in the present figures, for joining up with connection pipes running to a liquid bottle on the one hand and the body of the patient on the other hand.

The backup wall 3, placed on the radially outer side of the rollers 6, is curved as part of a circle with an angle which, in the present working example, may be about 100°, that is to say a little greater than the angle of 90° between the equally spaced rollers 6, this making certain that the pipe element 1 is nipped or squeezed at the start of the working part 8 shortly before the roller 6 at the end of the working part 8 has come clear of the backup wall 3 and so stopping its nipping effect on the pipe element. For this reason, it is not possible for any liquid to make its way backwards through the pipe element, while on the other hand, in normal operation the working part 8 of the pipe element is only nipped by one of the rollers 6 in its pumping position so that there are no undesired reactions between rollers acting on the pipe element at the same time.

The system for driving the wheel 5, which like the rollers 6 thereon may be made of synthetic resin, makes use of an electric motor 13 powered by batteries or the like not to be seen in the figure and which are placed in the space 14 on the two sides of the electric motor 13, with which they may be joined up by way of a control circuit (not to be seen in the figure) for adjustment of the speed of the electric motor 13, as will be known to those trained in the art. The electric motor 13, the support wheel 5 and the support part 2 are all supported on a plate 15, best made of metal, of U-like form. As will be seen more specially from FIG. 2, the flat middle part 16 of the plate 15 has a support sleeve 17 fixed to it, for example by screwing or by spot welding. This sleeve 17 has a plain bearing 18 therein for supporting a stub shaft 19 in which the wheel 5 is fixed. Wheel 5 has a great enough axial size to be so fixed to the stub shaft 19 that there is no danger of it being rocked on the shaft. In the present working example the wheel 5 is made up of two round plates 5a and 5b as walls thereof spaced by concentric spacer rings 5c and 5d, all made of synthetic resin. At their outer edges such plates 5a and 5b are joined up with pins 61 on which the rollers 6, made for example of hard rubber, are bearinged.

The top wing 20 in the figure of U-like plate 15 has the electric motor 13 fixed to its outer side, with the batteries (not figured) on the two sides of the electric motor. Wing 20 has a hole for the output shaft 13a of the electric motor 13 or a further piece of shaft fixed on such shaft, on which, on the inner side of wing 20, there is keyed a pinion 21 meshing with teeth 22, which are radial with respect to the axis 4 of turning of the wheel 5, on the outer side of the inner plate 5b at its outer edge. By a simple gearing system, with straight teeth, trouble-free transmission of power is possible with a high step-down ratio between pinion 21 and teeth 22 of for example 1:600 so that the electric motor 13 may be run at a high speed for which it is designed, without any complex gear system, such high running speed of the motor being stepped down to the very much lower speed of wheel 5. By supporting the driving shaft 13a of electric motor 13, for example in the sleeve or the like in the wing 20, pinion 21 may be well supported without any bearing at its end furthest from the electric motor 13, so that there is no chance of the pinion 21 being pushed from side to side. In fact, the design is such as to make quite certain that the desired driving force is transmitted by pinion 21 to the wheel 5. The axis of the driving shaft 13a and, for this reason, the main direction of the body of the electric motor, which is of a design generally on the market, and the general directions of the bodies of the batteries placed in space 14 on the two sides of the electric motor 13, are normal to the axis 4 of turning of wheel 5, that is to say parallel to the general direction of its body. For this reason, all the larger parts of the system are placed parallel to each other and even if the diameter of the wheel 6 is very large in size, as will be needed for smooth, quiet running at a low speed, the peristaltic pump will be very thin, as will be seen from the figures. The breadth of the peristaltic pump from side to side will be generally dependent on the diameter of the wheel 5 together with the thickness of the pipe element 1 so that even although the wheel 5 is, as desired, as large in diameter as possible, the peristaltic pump will not be unnecessarily broad. Furthermore, the present design, as is to be seen from the figure, makes it possible for the peristaltic pump to have a flat rectangular casing 12 with very much the right desired properties of a pump to be taken around by the patient with him, it being fixed for example on his belt or the like, resting flat against his body.

Support part 2, having on its inner side the part circular backup wall 3, may be moved in the support direction marked by the two-headed arrow 23 and is fixed to guide pins 24 running in the lower wing 25 of U-like part 15 so that motion of support part 2 in the direction of arrow 23, that is to say generally normal to the axis 4 of turning of the wheel 5, is possible. For nipping the pipe element 1 at the squeezing point 9 where one of the rollers 6 is pushed against the pipe element, support part 2 is acted upon by springs 26 pushing it towards the axis 4 of turning of wheel 5 with such a force that the desired nipping force, necessary for stopping free flow through the pipe element, takes effect on pipe element 1 in the working part 8 at the rollers 6, taking into account the stiffness of the material of the pipe element 1 and the pumping head or force. The pipe element 1 may well be made of silicone resin with an inner diameter of 3 to 4 mm and a wall thickness of 1 to 1.1 mm so that, given a force of spring 26 acting on the support part 2, between roughly 2 Newtons and 4 Newtons a pumping head of about 0.5 bar or somewhat more may be produced. At a speed of turning of wheel 5 between 25 and 240 rph, the upper limit of the pumping rate will be 250 ml/h, high enough for all purposes and more specially enteral nitrition or feeding. If desired, the pumping rate may be decreased to about one tenth of this rate. Taking into account the step-down ratio of 1:600 between the pinion 21 and the teeth 22, in this range of speed adjustment motor speeds between 180 and 250 rpm will come into question so that as the electric motor 13 any desired mass produced DC motor may be used. In view of the low running speed of wheel 5 with a diameter of at least 50 and in the present example about 70 mm or even more, the noise level will be very low, that is to say about 20 dB or even less so that in fact the only noise, generally speaking, will be soft purring of the electric motor 13 which furthermore will seem to be quieter because of casing 12.

Casing 12 is made in two parts, that is to say a top casing part 12a and a lower casing part 12b which have grip hollows 12c so that the two parts may be pulled clear of each other. On taking off the housing part 12b, which is lower down in the figure, the working part 8 of pipe element 1 will be uncovered and may be got at from the outside. When the support part 2 is pushed against the force of springs 26 towards lower wing 25 of U-like part 15, the pipe element will no longer be nipped by the roller 6 at the position 9 at which the roller is placed, so that the pipe element 1 will be resting more or less completely loosely against the inner side of the backup wall 3. In this respect, the amount of possible motion of support part 2 (along the direction marked by the two-headed arrow 23) against the force of springs 26 is so great that pipe element 1 may be moved completely clear of the nipping roller at 9; in fact, the amount of motion of the support part is somewhat greater than the inner diameter of the pipe element 1.

For trouble-free attention to the pipe element, for example for putting in a new piece of pipe or some other purpose with the support part 2 pulled back, the same may be locked in its pulled-back position for working on the pump and in the present working example it will be seen that a spring tonguepiece 27 is fixed on wing 25, tonguepiece 27 having a hook 28 or the like and having the tendency of springing into a position in which hook 28 comes into position to the back of a stop face 29 on support part 2 for locking the support part in the pulled-back position for making adjustments or doing some form of upkeep work on the pump. If the springing tonguepiece 27 is moved against its spring force, the hook 28 will be cleared from stop face 29 so that the support part 2 may be moved by the springs 26 back towards the axis 4 of turning of the wheel 5 into the working position of the pump parts. For moving the hook free of the stop face 29, there is an unlocking part 30 in the form of a pin running through support part 2, which may be pushed in from the front side of the support part 2, its opposite end then pushing the springing tonguepiece 27 clear of the stop face. For stopping operation of the peristaltic pump while the support part 2 is in the pulled-back position for adjustment of the pump, in which case there would be no pumping effect, the front end 30a of the unlocking part 30 is so placed that, when the casing is shut, it is forced inwards by the casing wall 12d (in the present example is part of the lower casing part 12b) and pushed inwards. Because of this, the springing tonguepiece 27 is forced back into its position freeing the stop face 29. For stopping the edge of casing wall 12d jamming against the end of unlocking part 30 on shutting the casing, the front end 30a of unlocking part 30 may be sloped at 30b or specially formed in some other way.

For this reason, when the casing part 12b is pulled off, the working part 8 of the pipe element 1 will be uncovered and in this position the support part 2 may be pulled back into the adjustment position and locked automatically by the hook 28 hooking onto the stop face 29, the springing tongue-piece 27 then forcing the unlocking part 30 to the left (in view of FIG. 2) so that its front end 30a is sticking out far enough; that is to say when the lower casing part 12b is put on again, the unlocking part 30 will be forced back again because of the casing wall 12d acting on the sloping face 30b of the said unlocking part 30, the springing tonguepiece 27 then being bent back and then kept in position, the stop face 29 at the same time being let go of by hook 28. In this operation position the support part 2 and, for this reason, the backup wall 3 will have the effect of forcing the pipe element 1 against the rollers 6 and at the nip point 9, without being dependent on manufacturing tolerances or the like. The force of the springs 26 in this respect may be changed as desired. The design makes it possible, in a simple way, on the one hand to see that there are no overgreat nipping or squeezing forces on the pipe element 1 at the nip point 9 while on the other hand, however, the desired force or pressure is on hand all the time to make certain that the pipe element 1 is shut completely by the nipping effect at the nip 9.

Taking a general view, it will be seen that the invention makes possible a peristaltic or roller pump which has quiet running properties, a low weight and a low volume so that patients, for example, undergoing enteral nutrition, may take it around with them all the time without in any way getting in their way causing any undesired effects in other respects. One form of the peristaltic pump with the pumping rates etc. as noted in the present specification has a size of the casing 12 measuring 146 mm ×64 mm ×35 mm, it keeping to all conditions with respect to exact rate control of the nutrient liquid as dependent on the speed of turning.

We claim:

1. In a peristaltic pump for medical purposes having a peristaltic flexible pipe element, a part-circular backup wall having an inwardly curved face for supporting said pipe element, a wheel with rollers for rolling said pipe elements and nipping it against said wall at a point moving along side pipe element giving a peristaltic pumping effect, and an electric motor for driving said wheel, characterized in that the wheel has an axis of turning normal to the axis of turning of said electric motor, the wheel has a gear teeth at an outer edge thereof, the electric motor has a pinion for driving said teeth with a step-down ratio of more than 1:100, the wheel has a stub shaft, there is an U-like part with a middle part in which said stub shaft is journalled, there is a wing on said U-like part supporting said electric motor, said pinion is on an inner side of said wing and there is a second wing at an opposite end of said U-like part for supporting said backup wall movingly thereon.

2. Peristaltic pump for medical purposes, especially for enteral nutrition or feeding, having a peristalic flexible pipe element co-operating along a part of its length with rollers supported on a wheel driven by an electric motor with the rollers nipping the pipe element against a part-circular backup wall giving a peristaltic pumping effect, with said motor and wall being arranged on opposite sides of the axis of rotation of said wheel and said axis being disposed normal to the axis of said motor, characterized in that said wheel, motor and wall are mounted to a common support part, said wheel has gear teeth at an outer peripheral portion thereof, said gear teeth are disposed in a substantially radial plane with respect to said axis of rotation of said wheel, said electric motor drives a pinion meshing with said gear teeth, a stub shaft is on said wheel, the support part is U-like with a middle part to which said stub shaft is journalled, a wing is on an end of said middle part supporting said electric motor with said pinion being on an inner side of said wing and including a second wing at an opposite end of said middle part for supporting said backup wall movingly thereon.

3. Peristalic pump as claimed in claim 2, characterized in that the electric motor drives the wheel with a step-down ratio of more than 1:100.

4. Peristaltic pump as claimed in one of claims 1 and 2, characterized in that the pump is enclosed in a housing defining enclosed spaces on opposite sides of the electric motor for the reception of motor-powering batteries.

5. Peristaltic pump as claimed in one of claims 1 and 2, characterized in having a spring for loading said backup wall and urging it towards the rotational axis of said wheel for causing the desired nipping of said pipe element.

* * * * *